(12) United States Patent  
Kim et al.

(10) Patent No.: US 6,702,734 B2  
(45) Date of Patent: Mar. 9, 2004

(54) SELF-PROPELLED ENDOSCOPIC MICRO-ROBOT AND SYSTEM FOR INTESTINAL ENDOSCOPY USING THE SAME

(75) Inventors: Byungkyu Kim, Seoul (KR); Young Mo Lim, Kyunggi-do (KR); Jinhee Lee, Seoul (KR); Jisang Park, Seoul (KR); Soo Hyun Kim, Taejon (KR); Jong-Oh Park, Seoul (KR)

(73) Assignee: Korea Institute of Science and Technology, Seongpuk-gu (KR)

( * ) Notice: Subject to any disclaimer, the term of this patent is extended or adjusted under 35 U.S.C. 154(b) by 87 days.

(21) Appl. No.: 09/993,850

(22) Filed: Nov. 14, 2001

(65) Prior Publication Data

US 2002/0111535 A1 Aug. 15, 2002

(30) Foreign Application Priority Data

Feb. 10, 2001 (KR) .......................................... 2001-6630

(51) Int. Cl.[7] .................................................. A61B 1/01
(52) U.S. Cl. ...................................... 600/114; 604/95.01
(58) Field of Search ........................ 600/114–116, 127, 600/129, 150, 152; 604/95.01

(56) References Cited

U.S. PATENT DOCUMENTS

| | | | | |
|---|---|---|---|---|
| 4,903,784 A | * | 2/1990 | Glaser | 173/121 |
| 5,398,670 A | * | 3/1995 | Ortiz et al. | 385/119 |
| 5,906,591 A | | 5/1999 | Dario et al. | |
| 6,162,171 A | | 12/2000 | Ng et al. | |
| 6,332,865 B1 | * | 12/2001 | Borody et al. | 356/241.1 |
| 6,440,061 B1 | * | 8/2002 | Wenner et al. | 600/114 |

* cited by examiner

Primary Examiner—John Mulcahy  
(74) Attorney, Agent, or Firm—Laurence S. Roach, Esq.; Jaeckle, Fleischmann & Mugel, LLP (57) ABSTRACT

A self-propelled endoscopic micro-robot, comprising a head for obtaining the errorless information of an interior of a tubular organ; an impact force generating unit connected the head generating an impact force according to a pneumatic pressure externally supplied and sucked by a air pressure supplier and making the self-propelled endoscopic micro-robot move in the tubular organ; and a plurality of supporting arms connected the head with end of the impact force for covering the impact force generating unit, making a housing of the self-propelled endoscopic micro-robot, and adjusting frictional force between the interior of the tubular organ and the housing as desired.

23 Claims, 7 Drawing Sheets

SELF-PROPELLED ENDOSCOPIC MICRO-ROBOT AND SYSTEM FOR INTESTINAL ENDOSCOPY USING THE SAME

CROSS-REFERENCE TO RELATED APPLICATIONS

This application claims the benefit of Korean Patent Application Serial No. 2001-6630, filed Feb. 10, 2001.

BACKGROUND OF THE INVENTION

1. Field of the Invention

The present invention relates to an intestinal endoscopic apparatus and system. More particularly, the present invention relates to a self-propelled endoscopic micro-robot that moves in a tubular organ or intestine by an internally-generated impact force, and that obtains precise information of the interior of the tubular organ or intestine.

2. Description of the Prior Art

Generally, endoscopes are useful medical devices for inspecting and examining the interior of tubular organs, such as a colon, that are otherwise inaccessible to examination by a physician or other healthcare provider. The endoscopic examination is a procedure requiring highly skilled techniques. The endoscopic technique was developed to reduce the necessity of surgical operations in the course of diagnostic procedures, to reduce patient discomfort, and to reduce recovery time and possible side effects.

The robot of the present invention has an autonomous ability to move within the tubular organs of a patient and to adapt its configuration to that of the surrounding environment. As an example, an endoscopic robot according to the prior art, designed for being inserted into the tubular organ such as an intestine of the patient and advanced therein in a prefixed direction with a so-called inchworm-like motion, moves in the intestine by pulling or sucking the interior walls of the intestine and obtains the images of the intestine.

The inchworm-like motion of the prior art endoscopic robot does not always enable trouble-free movement in the intestine. Particularly, in a problematic or a very angulated region of an intestine a conventional endoscopic robot may not easily advance and pass. Although the conventional robot may pass the problematic area, damage to or even rupture of the intestine walls may result.

In addition to the shortcomings above, use of a conventional endoscopic robot may require an endoscopist or a physician to distinguish between damage caused by the endoscope and the disease, a process which requires additional diagnostic time and thereby increases the time during which the patient must undergo examination and discomfort.

SUMMARY OF THE INVENTION

One object of the present invention is to provide a self-propelled endoscopic micro-robot that is propelled in forward and backward directions by an internally-generated impact force and which obtains precise information of the interior of the tubular organ or intestine without any damage to the walls.

Another object of the present invention is to provide a system for intestinal endoscopy obtaining precise information of an interior of the tubular organ or intestine using a self-propelled micro-robot that is propelled through the tubular organ or intestine in forward and backward directions by an impact force generated within the robot by a propulsion piston that is moved within a cylinder of the robot by an alternating source of pressurized air.

In order to accomplish the object, the present invention provides a system for intestinal endoscopy, comprising: a air pressure supplier for generating a predetermined pressure; and a self-propelled endoscopic micro-robot with which a air pressure supplier is externally connected capable of moving in a tubular organ without any damage to the tubular organ by an impact force generated by a pneumatic pressure provided and sucked by the pneumatic pressure supplier, and obtaining precise images of the interior of the tubular organ.

In order to accomplish the above objectives, the present invention provides a system for intestinal endoscopy, including an air pressure supply and a self-propelled endoscopic micro-robot. The air pressure supply generates an alternating pneumatic pressure that is supplied to the robot. The robot is propelled through the tubular organ by an impact force generated within the robot by the alternating pneumatic pressure. The robot moves in the tubular organ without damage thereto and obtains precise images of the interior of the tubular organ.

In order to accomplish the other object, the present invention provides a system for internal endoscopy, comprising: 1) a self-propelled endoscopic micro robot for intestinal endoscopy, including: (a) a photographing unit for photographing an interior of a tubular organ; (b) an illuminating unit provided on said photographing unit for illuminating the interior of the tubular organ; (c) a pneumatic actuator including a pneumatic cylinder, with a propulsion piston movably set within the pneumatic cylinder, said cylinder having a plurality of holes on its sidewall, and said propulsion piston pneumatically coming into collision with either end wall of the pneumatic cylinder to generate a propulsion force; (d) a damper for protecting the photographing unit from propulsive impact force generated by the propulsion piston; and (e) a plurality of linear actuators set between the photographing unit and the pneumatic cylinder actuator, wherein said actuators are adjustable in their lengths as desired; and 2) a pneumatic pressure supply unit connected to the pneumatic cylinder actuator of said robot through a hose, and selectively feeding pressurized air into the pneumatic cylinder of the pneumatic cylinder actuator to move the self-propelled endoscopic micro robot.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE INVENTION

Figure 1:
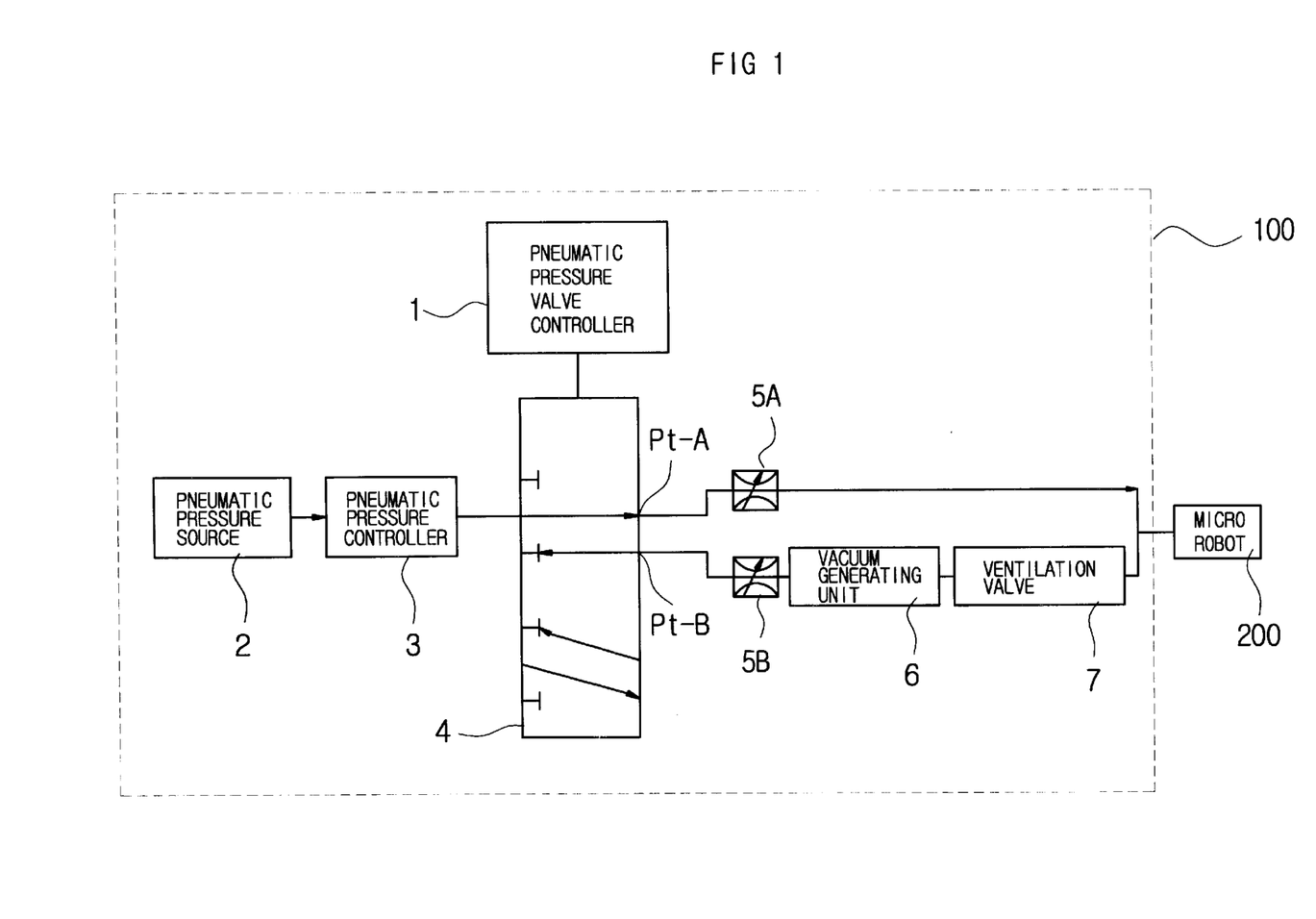
FIG. 1 is a schematic diagram showing a system for intestine endoscopy in accordance with the present invention.

FIG. 1 is a schematic diagram showing a system for intestine endoscopy in accordance with the present invention, which comprises a air pressure supplier 100 and a self-propelled endoscopic micro-robot 200 operating according to the control of the air pressure supplier 100 connected therewith.

As shown in the drawing, the air pressure supplier 100 comprises a pneumatic pressure supplying source 2 for generating a pneumatic pressure with a predetermined pressure, a pneumatic pressure controller 3 for controlling the pneumatic pressure from the pneumatic pressure supplying source 2, a pneumatic pressure valve 4 for switching direction of the pneumatic pressure via ports Pt-A and Pt-B, a pneumatic pressure controller 1 for controlling the pneumatic pressure valve 4 and a ventilation valve which will be explained later, first and second throttle valves 5A and 5B for controlling flow rate between the pneumatic pressure valve 4 and the self-propelled endoscopic micro-robot 200, a vacuum generating unit 6 connected to the second throttle valve 5B for sucking pneumatic pressure from the self-propelled endoscopic micro-robot 200, and a ventilation valve 7 connected to the vacuum generating unit 6 for outwardly exhausting the pneumatic pressure from the self propelled-endoscopic micro-robot 200, which is generated by the operation of the vacuum generating unit 6.

Also, the construction of the self-propelled endoscopic micro-robot 200 will be explained referring to the following drawings.

Figure 2:
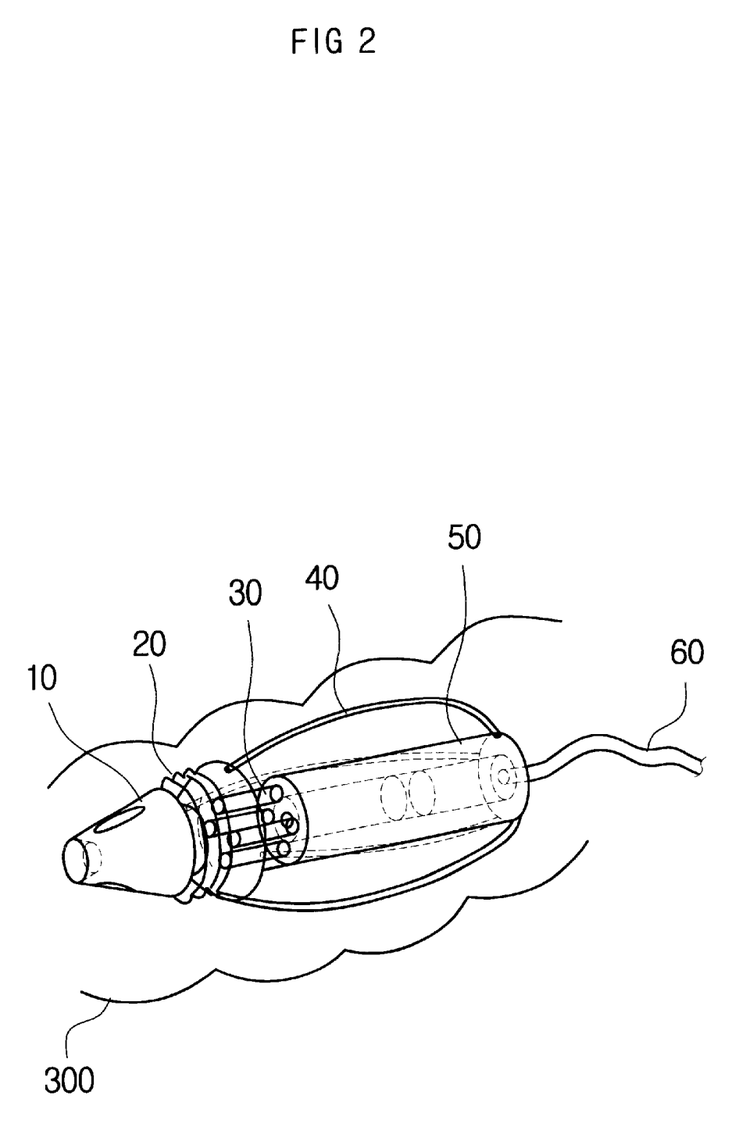
FIG. 2 is a perspective view showing a self-propelled endoscopic micro-robot in accordance with the present invention.
Figure 3:
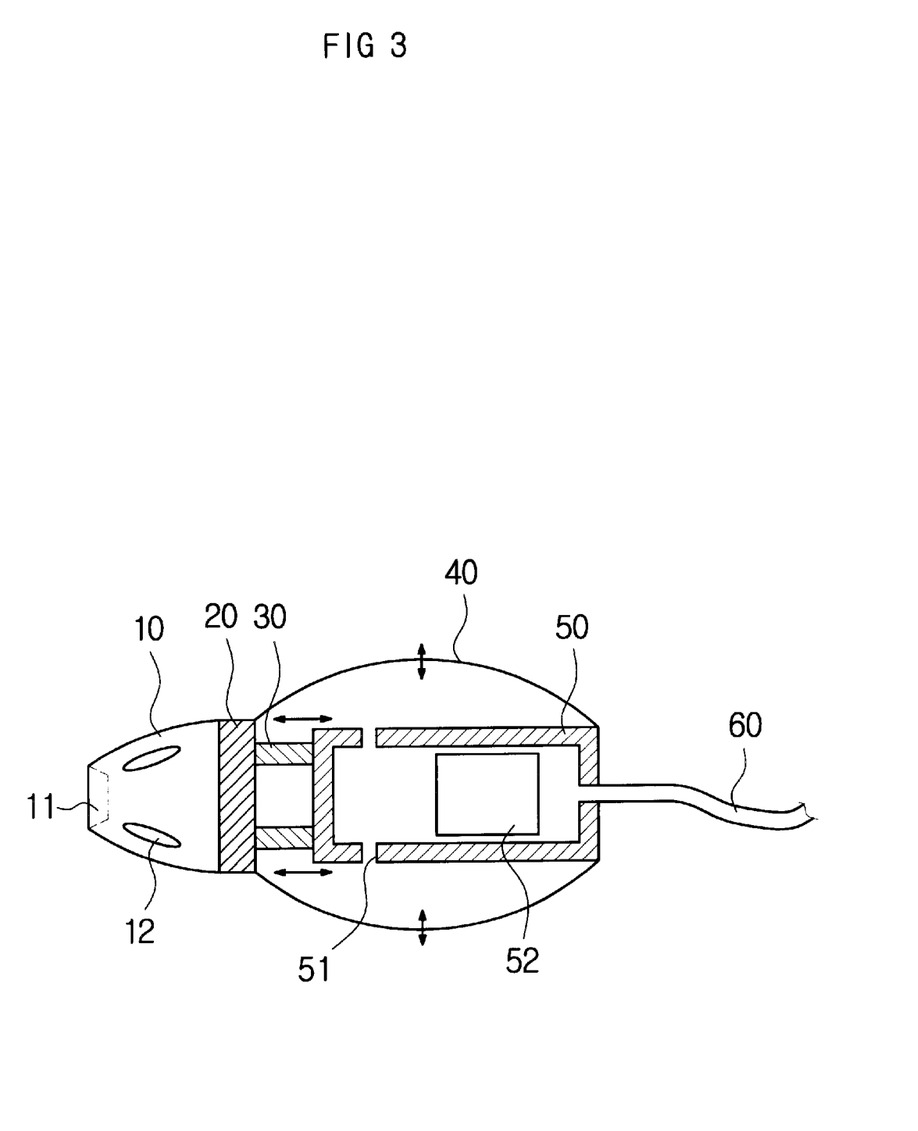
FIG. 3 is a sectional view showing the self-propelled endoscopic micro-robot in accordance with the present invention.

FIG. 2 is a perspective view showing a self-propelled endoscopic micro-robot in accordance with the present invention and FIG. 3 is a sectional view of FIG. 2.

As shown in the drawings, the self-propelled endoscopic micro-robot 200 comprises a head 10 with a light emitting unit 12, for example a light emitting diode (LED), for lighting the interior of a intestine 300 and with a camera 11 for taking images of its interior, in order to move the self-propelled endoscopic micro-robot 200, a cylinder 50 including a propulsion piston 52 therein for generating an impact force as the propulsion piston 52 is moved forward and backward and collided into either wall of the cylinder 50, a damper 20 connected to the head 10 for reducing the impact from the cylinder 50 and for protecting the head 10, a plurality of linear actuators 30 installed between the damper 20 and the cylinder 50 controlling moving direction of the self-propelled endoscopic micro-robot 200 as their lengths independently varied, a hose 60 connected to the cylinder 50 for passing air between the cylinder 50 and the air pressure supplier 100, a plurality of flexible arc-shaped supporting arms 40 connected to an end of the damper and to an end of the cylinder 50 for covering the linear actuators 30 and the cylinder 50, making a housing of the self-propelled endoscopic micro-robot 200, and adaptively adjusting friction between the interior of the tubular organ and the housing as the diameter of the intestine 300 so as to easily move in the intestine 300, particularly narrow regions having haustral folds.

Here, the damper 20 reduces the impact generated by the propulsion 52 in the cylinder 50 and protects the camera 11 and the light emitting unit 12 in the head 10 from it, and makes the micro-robot 200 provide the precise information of the interior of the intestine 300.

The flexible arc-shaped supporting arms 40 (for example, four) of are made of flexible material to adaptively change their shapes (dependent on their lengths, twists or bending) by the control of the linear actuators 30, which makes the self-propelled endoscopic micro-robot 200 move easily and freely in the interior of the intestine 300. That is, when the self-propelled endoscopic micro-robot 200 moves in the bent region of the intestine 300, the flexible arc-shaped supporting arms inside the bent intestine bend to the inside interior while those outside relatively extend, thereby the micro-robot 200 can smoothly and flexibly move in the bent intestine without any damages to the walls.

The linear actuators 30 independently control the flexible arc-shaped supporting arms 40 that the self-propelled endoscopic micro-robot 200 smoothly and flexibly moves in the intestine 300 regardless of its curvature. Namely, the linear actuators 30 vary their lengths according to the voltages applied thereto, thereby the flexible arc-shaped supporting arms 30 change their diameter at the radial direction of the body of the micro-robot 200, and at the same time, the self-propelled endoscopic micro-robot 200 varies its length along the direction of the intestine 300.

The variations of the flexible arc-shaped supporting arm 30 relates to the magnitude of the frictional force between the micro-robot 200 and the interior of the intestine 30. Therefore, if the frictional force is controlled to be relatively small, then the micro-robot 200 smoothly and flexibly steers in the intestine 300 even though it is very angulated or narrow. If the frictional force is adjusted to be relatively large by the variation of the flexible arc-shaped supporting arms 30 when the linear actuators 30 reduces their lengths, then the self-propelled endoscopic microrobot 200 does not move in the intestine against the frictional force.

The linear actuators 30 in accordance with the embodiment of the present invention used materials such as a shape-memory alloy or a polymer.

Figure 4:
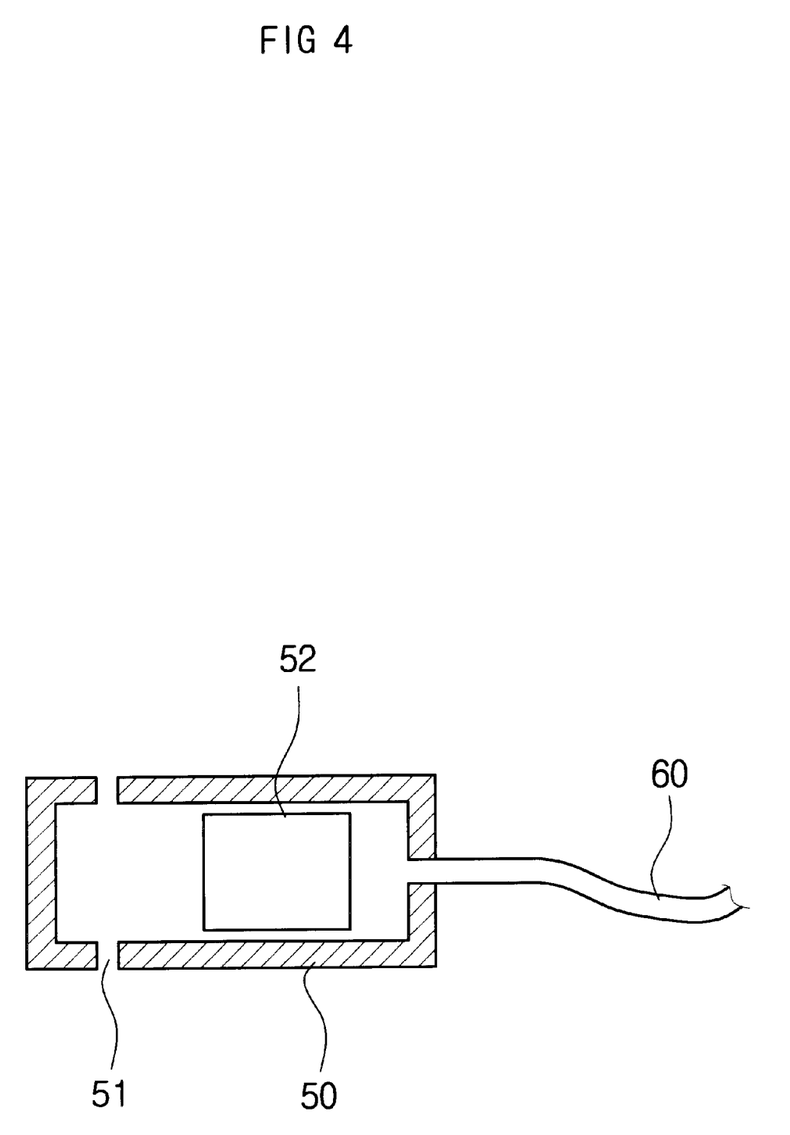
FIG. 4 is a sectional view of an actuator of the self-propelled endoscopic micro-robot.

FIG. 4 is a sectional view of an actuator of the self-propelled endoscopic micro-robot, which comprises a propulsion piston 52 for pneumatically coming into collision with either wall of the cylinder 50 to generate impact force according to the pneumatic pressure supplied or sucked by the air pressure supplier 100 and whereby moving the self-propelled endocsopic micro-robot 200 forward and backward in the intestine 300 and a plurality of holes 51 for inputting and outputting air, which is formed between the interior of the intestine 300 and a space of the cylinder opposite direction of a space of the cylinder 50 towards the air pressure supplier 100 with reference to the propulsion piston 52.

Figure 5A:
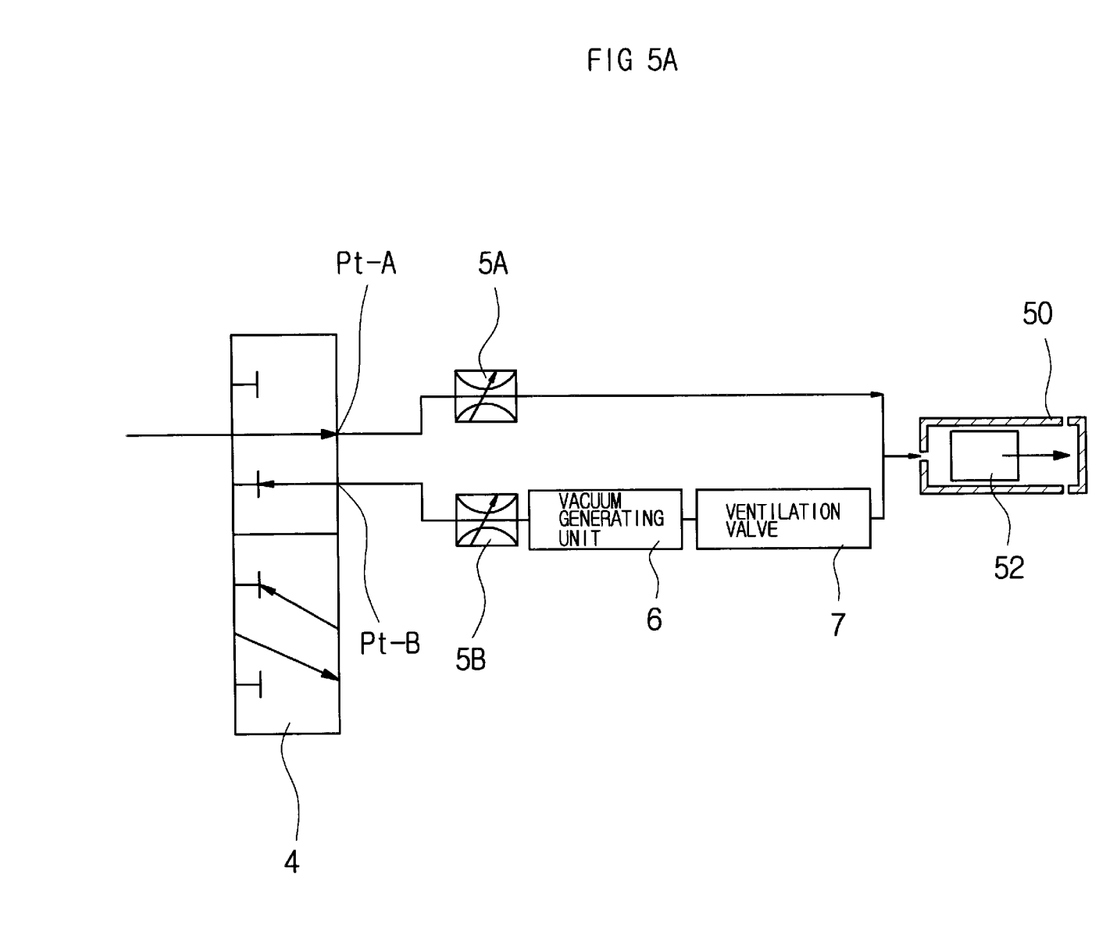
FIG. 5A is a schematic diagram for explaining a procedure when a air pressure supplier feeds pressurized air to the cylinder of the self-propelled endoscopic micro-robot.
Figure 5B:
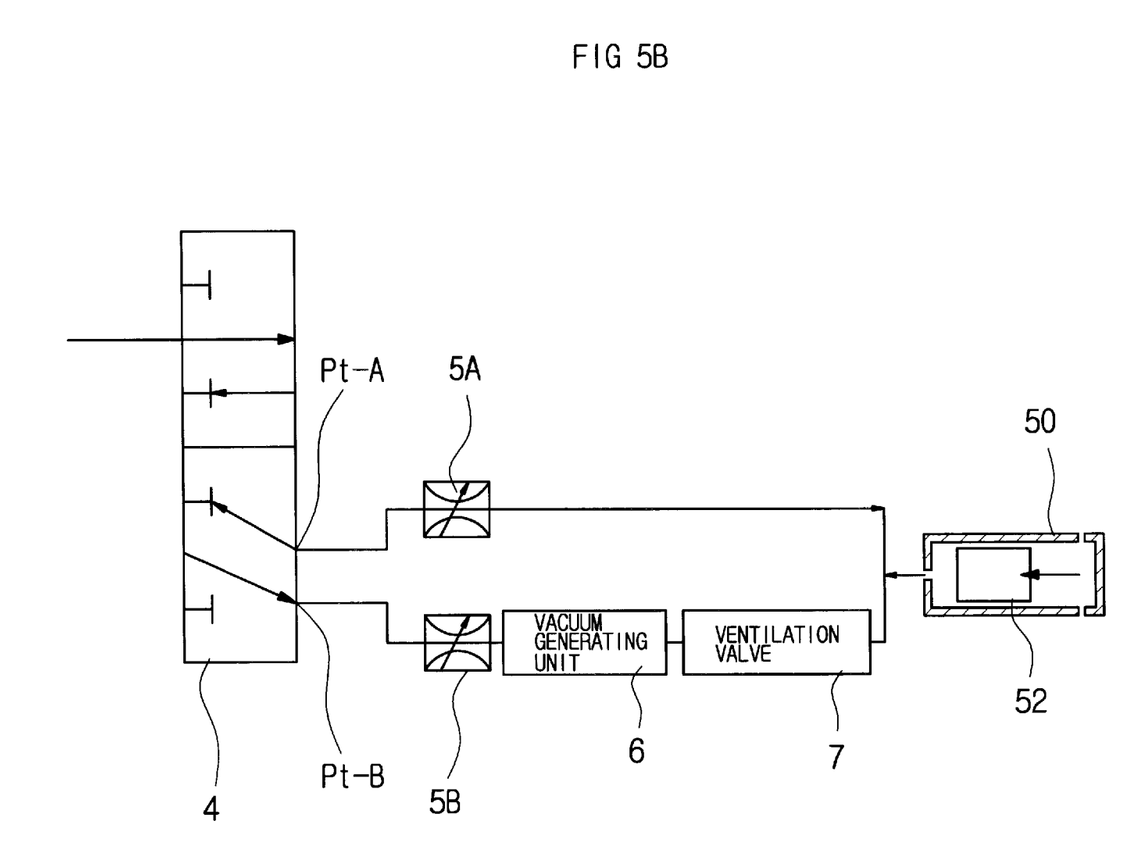
FIG. 5B is a schematic diagram for explaining a procedure when the pneumatic supplier sucks air from the cylinder of the self-propelled endoscopic micro-robot.

FIG. 5A is a schematic diagram for explaining a procedure when a air pressure supplier feeds pressurized air to the cylinder of the self-propelled endoscopic micro-robot and FIG. 5B is a schematic diagram for explaining a procedure when the pneumatic supplier sucks air from the cylinder of the self-propelled endoscopic micro-robot.

As shown in FIG. 5A, when the air pressure supplier 100 supplies air to the cylinder 50 of the self-propelled endoscopic micro-robot 200, then the propulsion piston 52 moves to the wall of the cylinder 50 towards the head 10. Namely, according to the control the pneumatic valve controller 1, if the port Pt-B of the pneumatic valve 4 is closed and the port Pt-A is opened, then the air from the pneumatic pressure source 2 outputs to the pneumatic pressure valve 4 and air flow rate throttle valve 5A and the air from the air flow rate throttle valve 5A inputs to the cylinder via the hose 60. Then, the propulsion piston 52 in the cylinder 50 moves to the wall of the cylinder 50 towards the head 10 and generates an impact force.

Therefore, the self-propelled endoscopic micro-robot 200 moves to the direction of the impact force if the impact force is relatively larger than the frictional force.

While the self-propelled endoscopic micro-robot 200 will not move to the direction of the impact force if the impact force is not large so as to overcome the frictional force.

As shown in FIG. 5B, if the air in the cylinder 50 is sucked by the air pressure supplier 100, then the propulsion piston 52 moves to the wall of the cylinder 50 towards the tail of the micro-robot 200.

As mentioned above, in order to the propulsion piston 52 returns to the wall of the cylinder 50 towards the tail of the micro-robot 200, the pneumatic valve controller 1 controls that the ports Pt-A and Pt-B are to be closed and opened, respectively. Then the air in the cylinder 50 is flowed to the ventilation valve 7 along the hose 60 by the pressure difference due to the operation of the vacuum generating unit 6 and discharged at the ventilation valve 7. Therefore, the propulsion piston 52 moves to the wall of the cylinder 50.

If the impact force is relatively larger than the frictional force, the self-propelled endoscopic micro-robot 200 moves to the direction of the impact force.

However, the self-propelled endoscopic micro-robot 200 will not move to the direction of the impact force if the impact force is not large so as to overcome the frictional force.

Here, the impact force by the forward and backward motions of the propulsion piston 52 depends on the pneumatic pressure and/or supplied air speed between the air pressure supplier 100 and the cylinder 50 as the first and second throttle valve 5A and 5B are controlled, respectively. Namely, amount and/or speed (i.e., flow rate) of the air supplied or sucked by the air pressure supplier 200 to/from the self-propelled endoscopic micro-robot 200 determines the step displacement of the self-propelled endoscopic micro-robot 200, and makes it freely and flexibly move in the interior of the intestine 300. For example, if the first throttle vale 5A is adjusted to flow a large amount of the air from the pneumatic pressure valve 4 to the self-propelled endoscopic micro-robot 200, thereby allowing the impact force towards the head 10 to be relatively larger than the frictional force between the self-propelled endoscopic micro-robot 200 and the wall of the intestine 300, and at the same time, if the second throttle vale 5B is adjusted to flow a small amount of the air from the vacuum generating unit 6 so that the air in the cylinder 50 is discharged through the ventilation valve 7, thereby allowing the impact force towards the tail of the micro-robot 200 to be relatively smaller than the frictional force between the self-propelled endoscopic micro-robot 200 and the wall of the intestine 300, then the self-propelled endoscopic micro-robot 200 moves forward.

Meanwhile, if the system is set contrary to the above conditions, then the self-propelled endoscopic micro-robot 200 moves backward.

Therefore, in the system for intestinal endoscopy in accordance with the present invention as constructed above, the self-propelled endoscopic micro-robot 200 is capable of moving in the interior of the intestine 300 forward and backward by the impact force when the propulsion piston 52 moves in the cylinder 200 forward and backward according to pneumatic pressure provided or sucked between the air pressure supplier 100 and the cylinder, and takes precise images of the interior of the intestine 300. Especially, the motion of the self-propelled endoscopic micro-robot 200 at the very angulated curve of the intestine will be explained referring to the drawing as below.

Figure 6:
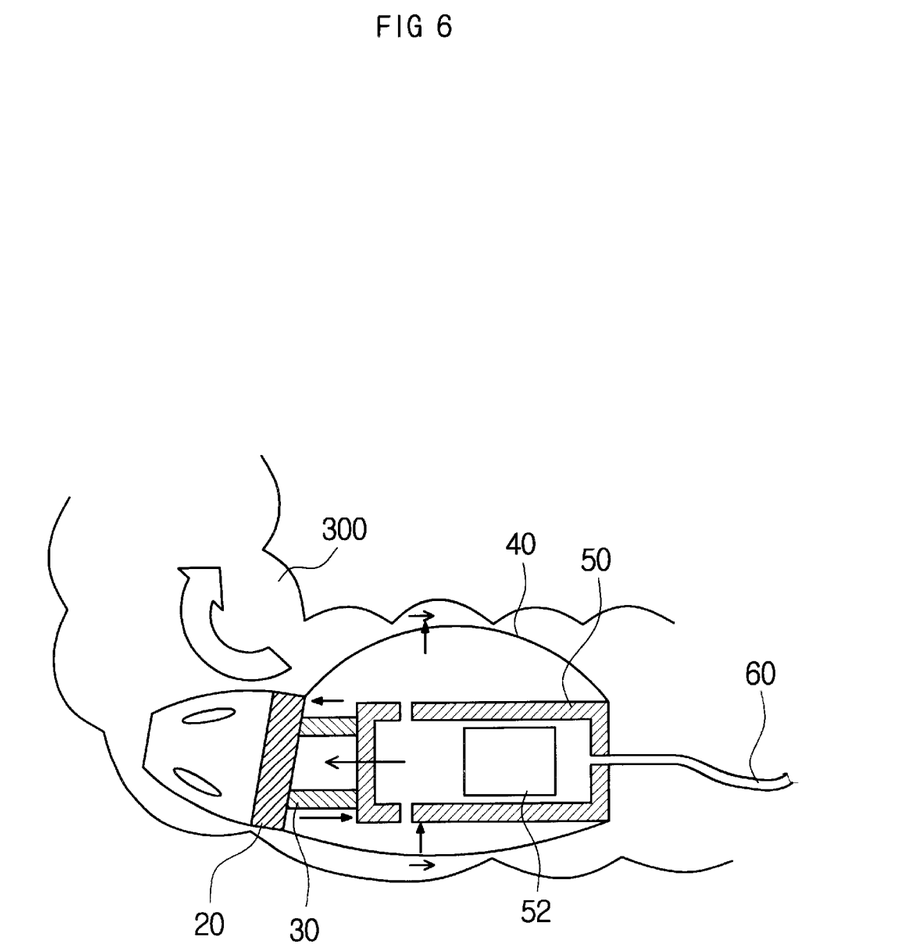
FIG. 6 is a sectional view for explaining a procedure that the self-propelled endoscopic micro-robot steers in the intestine.

FIG. 6 is a sectional view for explaining a procedure that the self-propelled endoscopic micro-robot steers in the intestine.

In order to move in the intestine 300 which is very angulated or bent from the lower part of the drawing paper to the upper, the self-propelled endoscopic micro-robot 200 adaptively changes its body size for adjusting the frictional force to fit the degree of the curve of the intestine 300 and passes the region. That is, when the head of the self-propelled endoscopic micro-robot 200 reaches the corner of the very angulated curve of the intestine 300, the lower linear actuators 30 as shown in the drawing paper extend their lengths and the upper linear actuators 30 as shown in the drawing paper shrink their lengths.

Then, the lower flexible arc-shaped supporting arms 40 are flat and the upper flexible arc-shaped supporting arm 40 are swollen as the lower linear actuators 30 expands relatively and at the same time the upper linear actuators 30 contracts, respectively.

Therefore, the body size or diameter of the self-propelled endoscopic micro-robot 200 is adaptively varied according to the degree of the curve for controlling the frictional force. Namely, if the head 10 of the self-propelled endoscopic micro-robot 200 is reached at the angulated intestine 300, then the flexible arc-shaped supporting arms 30 are relatively swollen and the other supporting arms 30 are relatively flat. Therefore, the self-propelled endoscopic micro-robot 200 can easily and flexibly move in the intestine without any damages to the walls regardless of the bent angle of the intestine.

Accordingly, as described above, the self-propelled endoscopic micro-robot in accordance with the present invention is capable of adaptively adjusting its sized or diameter according to the environments of the interior of the intestine, of easily and freely moving in the intestine without any damages to the walls and taking precise information of the intestine, even though the angulated curve of the intestine has α or γ loop.

Also, the system for intestinal endoscopy in accordance with the present invention is capable of providing complete information of the intestine without any damages to the walls using the air pressure supplier for supplying and sucking the air and the self-propelled endoscopic micro-robot connected to the air pressure supplier moving in the intestine by an impact force of the propulsion piston in the cylinder according to the supplied or sucked air.

Therefore, the self-propelled endoscopic micro-robot of the present invention effectively views and examines the interior of the intestine of a patient's body without causing damage or injury thereon.

In the embodiments of the present invention, even though the hose is mentioned as a path for flowing the air between the air pressure supplier and the cylinder, it is easy to appreciate that it can include the electrical wires to connect the electrical devices in the head with the others in the pneumatic pressure supplier.

Although a preferred embodiment of the present invention has been described for illustrative purposes, those skilled in the art will appreciate that various modifications, additions and substitutions are possible, without departing from the scope and spirit of the invention as disclosed in the accompanying claims.

What is claimed is:

1. A system for intestinal endoscopy, comprising:
   an air pressure supplier for generating a predetermined pressure; and
   a self-propelled endoscopic micro-robot with which said air pressure supplier is externally connected capable of moving in a tubular organ by an impact force generated by a pneumatic pressure provided and sucked by the air pressure supplier without any damage to the tubular organ, and obtaining precise images of the interior of the tubular organ.

2. The system according to claim 1, wherein said head comprises:
   a light emitting unit for lighting the interior of the tubular organ; and
   a camera for obtaining the precise images as the light emitting unit lighted the interior of the tubular organ.

3. The system according to claim 2, wherein said light emitting unit comprises a plurality of light emitting diodes.

4. The system according to claim 1, wherein said impact force generating unit comprises:
   a cylinder for generating the impact force by pneumatic pressure supplied and sucked by the pneumatic pressure supplier; and
   a plurality of linear actuators installed between the head and cylinder controlling the direction of the self-propelled endoscopic micro-robot.

5. The system according to claim 4, wherein said linear actuators comprises a shape-memory alloy or a polymer variable in length according to applied voltages thereto.

6. The system according to claim 4, wherein said cylinder comprises:
   a propulsion piston for pneumatically coming into collision with either wall of the cylinder to generate impact force according to the pneumatic pressure supplied or sucked by the air pressure supplier and making the self-propelled endocsopic micro-robot move forward or backward in the tubular organ; and
   a plurality of holes for inputting and outputting air, which are formed at a predetermined portion of the cylinder toward the head.

7. The system according to claim 4, wherein said system further comprises a damper installed between the head and the linear actuators for protecting the head from propulsive impact force generated by the propulsion piston.

8. The system according to claim 1, wherein said system further comprises a hose to flow the air between the impact force generating unit and the pneumatic pressure supplier.

9. The system according to claim 1, wherein said supporting arms are flexible arc-shaped bars bent from the self-propelled endoscopic micro-robot towards the tubular organ.

10. The system according to claim 1, wherein said air pressure supplier comprises:
    a pneumatic pressure generating unit for generating the pneumatic pressure;
    an air flow rate controlling unit for controlling the pneumatic pressure supplied and sucked to and from the self-propelled endoscopic micro-robot; and
    a pneumatic pressure controller for controlling the air flow rate controlling unit.

11. The system according to claim 10, wherein said air flow rate controlling unit comprises:
    a pneumatic pressure valve for switching direction of the pneumatic pressure between the pneumatic pressure generating unit and the self-propelled endoscopic micro-robot according to the control of the pneumatic pressure controller; and
    a plurality of air flow rate controlling valves for controlling air flow rate via the pneumatic pressure valve.

12. The system according to claim 10, wherein said flow rate controlling unit comprises:
    a plurality of pneumatic pressure flow rate controlling valves for controlling pneumatic flow rates inputted and outputted to and from the pneumatic pressure valve according to the control of the pneumatic pressure controller;
    a vacuum generating unit for sucking pneumatic pressure from the self-propelled endoscopic micro-robot; and
    a ventilation valve for outwardly exhausting the pneumatic pressure from the self-propelled endoscopic micro-robot, which is generated by the operation of the vacuum generating unit.

13. The system according to clam 1, wherein said impact force depends on the pneumatic pressure and applied speed thereof between the air pressure supplier and the self-propelled endoscopic micro-robot.

14. A self-propelled endoscopic micro-robot, comprising:
    a head for obtaining the errorless information of an interior of a tubular organ;
    an impact force generating unit connecting the head generating an impact force according to a pneumatic pressure externally supplied and sucked by a air pressure supplier and making the self-propelled endoscopic micro-robot move in the tubular organ; and a plurality of supporting arms connecting the head with end of the impact force generating unit for covering the impact force generating unit, making a housing of the self-propelled endoscopic micro-robot, and adjusting frictional force between the interior of the tubular organ and the housing as desired.

15. The self-propelled endoscopic micro-robot according to claim 14, wherein said head comprises:

a light emitting unit for lighting the interior of the tubular organ; and an information obtaining unit for obtaining the precise images as the light emitting unit lighted the interior of the tubular organ.

16. The system according to claim 15, wherein said light emitting unit comprises a plurality of light emitting diodes.

17. The system according to claim 14, wherein said impact force generating unit comprises:

a cylinder for generating the impact force by pneumatic pressure supplied and sucked by the pneumatic pressure supplier; and a plurality of linear actuators installed between the head and cylinder controlling a steering of the self-propelled endoscopic micro-robot.

18. The system according to claim 17, wherein said linear actuators comprises a shape-memory alloy or a polymer variable in length according to applied voltages thereto.

19. The system according to claim 17, wherein said cylinder comprises:

a propulsion piston for pneumatically coming into collision with either wall of the cylinder to generate impact force according to the pneumatic pressure supplied or sucked by the air pressure supplier and making the self-propelled endoesopic micro-robot move forward or backward in the tubular organ; and a plurality of holes for inputting and outputting air, which are formed at a predetermined portion of the cylinder toward the head.

20. The system according to claim 17, wherein said system further comprises a damper installed between the head and the linear actuators for protecting the head from propulsive impact force generated by the propulsion piston.

21. The system according to claim 14, wherein said system further comprises a hose to flow the air between the impact force generating unit and the pneumatic pressure supplier.

22. The system according to claim 14, wherein said supporting arms are round-typed bars bent from the self-propelled endoscopic micro-robot towards the tubular organ.

23. The system according to the claim 14, wherein said impact force depends on the pneumatic pressure and supplied speed thereof between the air pressure supplier and the self-propelled endoscopic micro-robot.

* * * * *